United States Patent [19]

Masilamani et al.

[11] Patent Number: 4,792,639

[45] Date of Patent: * Dec. 20, 1988

[54] PROCESS FOR THE PRODUCTION OF METHYL ETHERS FROM BRANCHED MONOOLEFINS

[75] Inventors: Divakaran Masilamani, Morristown; George S. Hammond, Madison; Andiappan K. S. Murthy, Lake Hiawatha, all of N.J.

[73] Assignee: Allied-Signal, Inc., Morris Township, N.J.

[*] Notice: The portion of the term of this patent subsequent to Nov. 24, 2004 has been disclaimed.

[21] Appl. No.: 90,175

[22] Filed: Aug. 27, 1987

Related U.S. Application Data

[62] Division of Ser. No. 781,163, Sep. 30, 1985, Pat. No. 4,709,101.

[51] Int. Cl.$^4$ ............................................. C07C 41/06
[52] U.S. Cl. .................................. 568/697; 568/671; 568/678
[58] Field of Search ..................... 568/697, 678, 671

[56] References Cited

U.S. PATENT DOCUMENTS 3,121,124  2/1964  Verdol .
4,198,530  4/1980  Wentzheimer et al. .
4,320,232  3/1982  Volkamer et al. .
4,454,356  6/1984  Masilamani et al. .
4,510,336  4/1985  Hearn .

Primary Examiner—Howard T. Mars
Attorney, Agent, or Firm—Richard C. Stewart; Gerhard H. Fuchs

[57] ABSTRACT

An improved process for the production of methyl ethers of the type in which methanol is reacted with a branched monoolefin in the presence of a catalytically effective amount of one or more acid catalyst, said improvements comprising carrying out said reaction in one or two steps in the presence of one or more liquid organic compounds having one or more hydroxy substituents which functions as a carrier for the branched monoolefins. The hydroxy compound also inhibits the polymerization of the branched monoolefins.

13 Claims, 1 Drawing Sheet

PROCESS FOR THE PRODUCTION OF METHYL ETHERS FROM BRANCHED MONOOLEFINS

This application is a division of application Ser. No. 781,163, filed 9/30/85 now U.S. Pat. No. 4,709,101.

BACKGROUND OF THE INVENTION

1. Field of the Invention

This invention relates to a process for the production of methyl ethers. More particularly this invention relates to such process in which methanol is reacted with a branched olefin in the presence of an acid catalyst and an additive which prevents or inhibits polymerization of the olefin.

2. Prior Art

Methyl ethers derived from branched monoolefins such as methyl-t-butyl ether are known additives to gasoline which improve the octane rating of mixtures. Such methyl ethers are produced by reacting methanol with isobutylene, or the corresponding higher branched monoolefin, in the presence of an acidic catalyst. The reaction can proceed with mixed hydrocarbon streams containing the branched monoolefin, with most catalytic systems being generally economically limited to hydrocarbon streams containing at least about 50% of the desired branched monoolefin, typically in combination with other monoolefins, diolefins and alkanes.

Among the common catalysts for the reaction are zeolites, acidic ion exchange resins and acidic inorganic materials. The reaction is normally conducted either in a batch fashion or with co-current feed of methanol and hydrocarbon. Unfortunately, the most common source of branched monoolefins, such as isobutylene, is from refinery operations wherein the isobutylene is present as less than 50% of a hydrocarbon stream, which often contain butadiene. While linear monoolefins and alkanes (e.g., butane) are inert in the presence of methanol and such acidic catalysts, the presence of butadiene complicates the reaction with most conventional catalysts, producing by-products such as polybutadienes.

U.S. Pat. No. 4,219,569 discloses a process of providing methyl-t-butyl ether (MTBE) suitable for gasoline-blending and C-4 hydrocarbons depleted of isobutylene suitable for alkylation. This patent indicates that simple distillation will not produce a C-4 overhead free of methanol in amounts objectionable for alkylation. Therefore, the patent recommends passing the distillate through a solvent such as ethylene glycol to lower its methanol content to below 100 ppm. This process suffers from a number of disadvantages. For example, the process is complex in that it requires a three step distillation and stripping the thus causing capital expense. Moreover, a fourth step (methanol stripping of the MTBE) is required, if a methanol content of less than about 5 weight % is required.

U.S. Pat. No. 2,720,547 describes a process in which mixed butenes are fed adjacent to the bottom of a reaction column operating at −50° C. to +50° C. and a mixture of methanol and alkanesulfonic acids are fed adjacent the top of the column. An overhead stream (containing unreacted butenes and a bottoms stream containing alkanesulfonic acid catalyst, methyl-t-butyl ether product and small amounts of methanol to which excess methanol is added) are both fed from the reaction column to a fractionating column operating at lower pressure. Four streams are removed from the fractionating column, one of which is an azeotrope of methyl-t-butyl ether and methanol. Methanol is scrubbed from the methyl-t-butyl ether with water.

U.S. Pat. No. 5,454,356 discloses a process for producing methyl ethers of branched monoolefins. In this process, methanol is reacted with branched monoolefins, such as isobutylene, or mixtures of hydrocarbons such as mixed C-4's from a refinery, in the presence of methanesulfonic acid. In this process the reactor also functions as a fractionator.

SUMMARY OF THE INVENTION

The present invention is directed to an improved process for the preparation of methyl ethers of branched monoolefins. More particularly, the process of this invention relates to an improved process of producing methyl ethers of branched monoolefins in which methanol is reacted with a branched monoolefin in the presence of an acid catalyst, the improvement comprises carrying out said reaction in a medium comprised of one or more liquid organic compounds substituted with one or more hydroxy groups, which compounds are herein referred to as "mono- and polyhydroxy compounds".

DETAILED DESCRIPTION OF THE PREFERRED EMBODIMENTS

Figure 1:
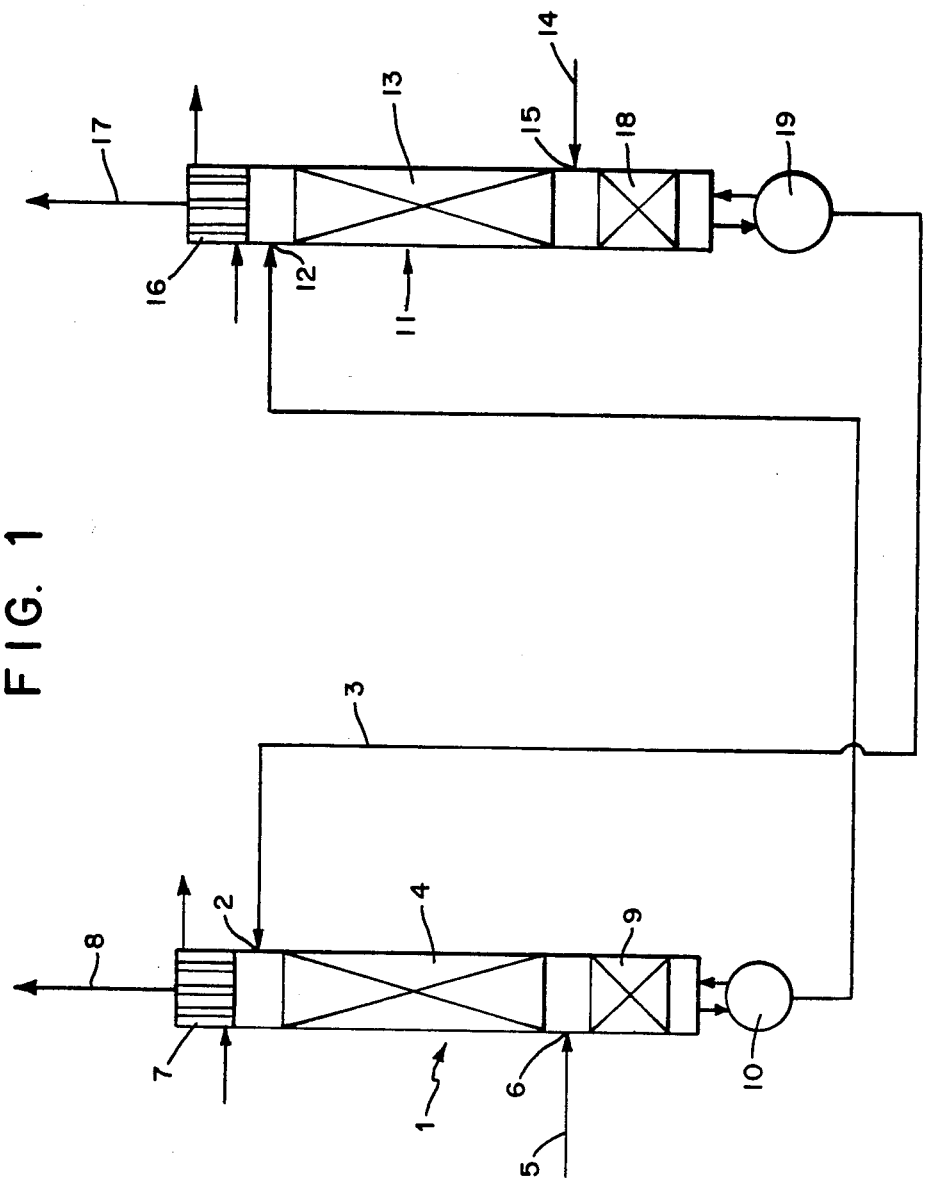
FIG. 1 is a simplified flow diagram illustrating a preferred two step procedure for carrying-out the process of the present invention.

In the process of this invention methanol and one or more branched monoolefins, are reacted in the presence of an acid catalyst and one or more liquid organic compounds substituted with one or more hydroxy substituents ("mono- or polyhydroxy compounds"). The process of this invention can be illustrated by the following reaction Scheme I:

Scheme I

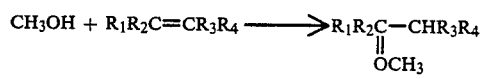

In general, the branched monoolefin and methanol are reacted in the presence of a "catalytically effective amount" of an acid catalyst and a "polymerization inhibiting amount" of one or more of mono or poly hydroxy compounds.

In the preferred embodiments of the invention, the process is carried out in two steps as shown in Scheme II:

Scheme II

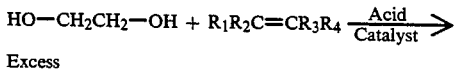

Excess

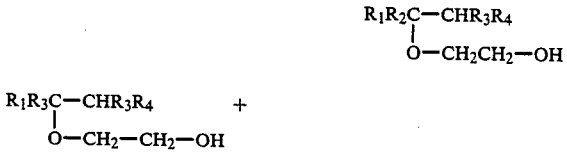

-continued
Scheme II

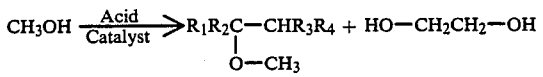

In the first step of the process, it is believed that the mono or polyhydroxy compound (ethylene glycol is used as an example in Scheme II) functions as a carrier for the monoolefin forming a high boiling monoether from which the other non-reacting olefins in the olefin stream are easily separated. In the two-step process shown in Scheme II, methanol is not contacted directly with the olefin stream. Thus, unreacted spent olefins are thus free of methanol and are suitable for alkylation. In the second step of the process, the high boiling monoether is contacted with methanol. Transetherification takes place to from the more volatile methylether from which the high boiling mono or polyhydroxy compound is easily removed.

In the above referenced schemes:

is a branched monoolefin in which $R_1$ and $R_2$ are the same or different and are alkyl; and $R_3$ and $R_4$ are the same or different and are hydrogen or alkyl.

As noted above, branched monoolefins having a branched point at a double bond are required. Branched isomers having no branch point at a double bond (e.g. 4-methylpentene-1,3-methylpentene-1,4-methylpentene-2,3-methylbutene-1) would not be expected to react to any appreciable extent, nor would conjugated diolefins.

Illustrative of useful branched monoolefins are:
2-methylbutene-1
2-methylbutene-2
2-methylpentene-1
2-methylpentene-2
3-methylpentene-2
2-ethylbutene-1
2,3-dimethylbutene-2
2,3-dimethylbultene-1
2,3-dimethylpentene-2
2,3-dimethylhexene-2
3,4-dipropylhexene-3
2-methyl-3-propylbutene-2
2-butylbutene-2
2,3-dimethylheptene-2
4,5-dipropylheptene-4
2-methyl-3-ethylpentene
4,5-diethylheptene-4
2-methyl-3-ethylheptene-2
4-propyl-4-methylephtene-2
2-methyl-3-ethylbutene-1.

In the preferred embodiments of the invention $R_1$ and $R_2$ are the same or different and are alkyl; and $R_3$ and $R_4$ are hydrogen. In the particularly preferred embodiments of the invention, $R_1$ and $R_2$ are the same or different and are alkyl having from 1 to about 7 carbon atoms; and $R_3$ and $R_4$ are hydrogen. In the most preferred embodiments of the invention, $R_1$ and $R_2$ are the same or different and are alkyl having from 1 to 3 carbon atoms, and $R_3$ and $R_4$ are hydrogen.

Especially useful monoolefins for use in the process of this invention are 2-methylpropene (isobutylene), 2-methylbultene-1 and 2-methylbutene-2, with 2-methyl propene being most preferred.

Useful branched monoolefins are frequently contained in hydrocarbon streams containing alkanes, other monoolefins and, sometimes, diolefins which stream are produced in refinery operations. Thus, for example, isobutylene is produced in refinery operations in admixture with 1-butene, 2-butenes, 1,3-butadiene, normal butane and isobutane. Additional components, including methane, ethane, ethylene, propylene and the like, may also be present. In such so-called C-4 fractions, there may also be trace amounts of pentenes, pentanes and pentadienes. In practicing the present invention, virtually all hydrocarbon streams in which the branched monoolefin is present in an amount of at least about 5 mole percent, and preferably at least about 10 mole percent can be used. In a typical refinery operation, the hydrocarbon stream is usually treated to remove lower hydrocarbons from the C-4 fraction, debutanized to remove butanes and distilled to remove butadiene. The hydrocarbon stream from any point in the treatment after the branched mono-olefin reaches a concentration of at least about 5 mol percent can be used in the practice of the process of this invention; from the crude steam at the cracking unit wherein the hydrocarbons are generated to the purified stream at a point after butadiene removal.

The process is carried out in the presence of a "catalytically effective amount" of one or more "effective acid catalysts." As used herein, "a catalytically effective amount" is an amount of the catalyst which is sufficient to catalyzed the reaction between methanol and the branched olefin to any extent. Specification of such amounts is well known to those of skill in the art and does not represent a part of this invention. Accordingly, the amounts used with methanol and any particular branched monoolefin will not be discussed herein in great detail. In summary, the amount of acid catalyst employed is at least about 0.1 mole percent based on the total moles of methanol. In the preferred embodiments of the invention, the amount of the acid catalyst will generally vary from about 0.1 to about 25 mole percent based on the total moles of methanol, and in the particularly preferred embodiments the amount of acid catalyst may vary from about 0.5 to about 15 mole percent on the aforementioned basis. Amongst these particularly preferred embodiments most preferred are those embodiments in which the mole percent of acid catalyst varies from about 1 to about 10 mole percent based on the total moles of methanol.

As used herein an "effective acid catalyst is any acid catalyst which will catalyze the reaction of methanol and a branched olefin to form the corresponding methyl ether. Useful acid catalysts are well known in the art and can vary widely. Preferred for use in the conduct of the process of this invention are sulfonic acid catalysts. Illustrative of useful and preferred sulfonic acid catalysts are aromatic sulfonic acids such as benzenesulfonic acid, m-nitrobenenesulfonic acid and the like, alkanesulfonic acids, such as methanesulfonic acid, ethanesulfonic acid, butanesulfonic acid, propanesulfonic acid and the like, and polymeric sulfonic acids such as sulfonated polystyrene, sulfonated poly(p-methylstyrene), sulfonated poly(p-methylstyrene), sulfonated poly(p-ethylstyrene) and the like. Alkane sulfonic acids and polymeric sulfonic acids are particularly preferred, and methanesulfonic acid and sulfonated polystyrene are most preferred.

The process is carried out in the presence of a "polymerization inhibiting effective amount" of one or more liquid organic compounds having one or more hydroxy substituents. As used herein, "a polymerization inhibiting effective amount" is an amount of the said hydroxy compounds which is effective in inhibiting the polymerization of the branched monoolefin to any extent. The amount of the hydroxy compounds, employed in any situation will depend on a number of factors, including the amount of methanol and acid catalyst employed and the particular hydroxy compound acid used. Normally, such an amount is an amount which in combination with methanol present in the reaction mixture is sufficient to provide a mole ratio of hydroxy moieties to acid moieties of at least about 2.75. In the preferred embodiments of the invention, the above-referenced mole ratio is at least about 3 to about 7, and in the particularly preferred embodiments is from about 3 to about 6. Amongst these particularly preferred embodiments, most preferred are those embodiments wherein the aforementioned mole ratio is from about 3 to about 5.

The type of mono- or poly-hydroxy compounds employed in the conduct of this invention can vary widely. Examples of such compounds are mono-hydroxy aliphatic and aromatic alcohols and phenols such as n-butanol, n-pentanol, n-hexanol, n-octanol, n-decanol, 2-propanol, 2-methyl-1-propanol, phenol, cyclohexanol, cyclopentanol, 2-butanol, 3-methyl-1-butanol, 2-methyl-2-propanol, benzylalcohol and the like and polyhydroxy aliphatic compounds such as ethylene glycol, propylene glycol, pentaerythritol, 2,3-dimethyl-2,3-butanediol, 1,2-diphenyl-1,2-ethanediol, trimethyleneglycol, dipropylene glycol, glycerol, 1,2-butanediol, meso and dl-2,3-butanediol, tripropylene glycol, tetrapropylene glycol, tetramethylene glycol, tetraethylene glycol, 1,4-butanediol, cis-1,2-cyclopentanediol, trans-1,2-cyclopentanediol, diethylene glycol, triethylene glycol, cis-1,2-cyclohexanediol, trans-1,2-cyclohexanediol and the like. Polyhydroxy aliphatic compounds are preferred for use in the process of this invention, and aliphatic diols and triols are particularly preferred. Amongst these particularly preferred embodiments most preferred as those in which the hydroxy compounds employed are diols such as the ethylene glycol and propylene glycols.

Reaction pressures are not critical and can be varied widely. For example, the process can be conveniently conducted at sub-atmospheric, atmospheric and super-atmospheric pressure.

Process temperatures are also not critical and can vary widely. Temperatures within the range of from about 0° C. to about 100° C. are preferred, and reaction temperatures of from about 25° C. to about 80° C. are particularly preferred. Above 100° C., dimethylether formation may begin to compete with formation of the desired methyl ether and process temperatures above the 100° C. are usually avoided.

The process of this invention is carried out over a period of time suficient to produce the desired compound in adequate yield. Reaction times are influenced to a significant degree by the reactants; the reaction temperature; the concentration and choice of reactants; and catalyst the choice and concentration of reaction solvent; and by other factors known to those skilled in the art. In general, residence times can vary from about a few minutes to 24 hours or longer. In most instances, when employing preferred reaction conditions, residence times will be found to vary from a few minutes to about 3 hours.

The process of this invention can be conducted in a batch, semicontinuous or continuous fashion. The reactants and reagents may be initially introduced into the reaction zone batchwise or they may be continuously or intermittently introduced in such zone during the course of the process. Means to introduce and/or adjust the quantity of reactants introduced, either intermittently or continuously into the reaction zone during the course of the reaction can be conveniently utilized in the process, especially to maintain the desired molar ration of the reaction solvent, reactants and reagents. The reaction can be conducted in a single reaction zone or in a plurality of reaction zones, in series or in paralled or it may be conducted intermittently or continuously in an elongated tubular zone or series of such zones. The materials of construction employed should be inert to the reactants during the raction and the fabrication of the equipment should be able to withstand the reaction temperatures and pressure.

The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing the reactions mixture can be employed. Mixing by vibration, shaking, stirring, rotation, oscillation, ultrasonic vibration or the like are all illustrative of the type of agitation means contemplated. Such means are available and well known to those skilled in the art.

The product methyl ether compound can be isolated from the reaction mixture and purified employing conventional techniques. Illustrative of such techniques are evaporation, distillation, solvent extraction and recrystallization. The preferred technique is distillation.

Reactants and reagents used in the process of this invention are readily available materials. Such materials can be conveniently prepared in accordance with conventional preparatory procedures or obtained from commericial sources.

Methyl ethers of branched chain monoolefins prepared in accordance with the process of this invention have many varied uses which are known in the art. For example, as disclosed in U.S. Pat. No. 4,218,569, certain of such ethers, as for example methyl-t-butyl ether, are useful in gasoline blending.

The following specific examples are presented to more particularly illustrate the invention are not to be construed as limitations thereon.

EXAMPLE I

FIG. 1 illustrates an embodiment of this invention which is carried out using two rectors. In FIG. 1 is depicted a reactor 1 into which ethylene glycol is introduced at point 2(a) via line 3 just above catalyst bed 4. Bed 4 is composed of a sulfonic acid resin. $C_4$ feedstock containing at least about 5–15 mole percent of isobutylene is introduced into reactor 2 via line 5 at point 6 just below bed 4. After introduction into reactor 1, the ethylene glycol percolates downward through bed 4, contacting the upward percolating $C_4$ feedstock in counter current fashion. In bed 4, the ethylene glycol reacts with the isobutylene in the feedstock, forming the corresponding mono-tert-butyl ether. The mole ratio of glycol/isobutylene is maintained at about six. Very little di-t-butyl ether is expected to be formed. Under these conditions, the equilibrium partial pressure of isobutylene over the bottom stream is less than that of the incoming isobutylene stream. The spend C4 depleted of isobutylene continues upward through the reactor and is refluxed using condenser 7 to eliminate carry over of ethylene glycol. The spent C4 is then vented via line 8.

The bottom stream consisting of excess ethylene glycol and its mono-t-butylether is stripped off of dissolved gases (in the absence of the catalyst in stripping section 9 and reboiler 10) and is introduced into a second reactor 11 at point 12 where it is contacted countercurrently with methanol in catalyst bed 13 composed of sulfonic acid resin. Methanol is fed to reactor 11 via line 14, and introduced into reactor 11 at point 15 and percolates upward into catalyst bed 13. Transetherification occurs in the catalyst bed 13 resulting in the formation of methyl-t-butylether (MTBE) and ethylene glycol. The low boiling MTBE (bp 56° C.) vaporizes upward from the catalyst bed 13 and is refluxed using condenser 16 to eliminate carry-over of ethylene glycol and methanol. The excess ethylene glycol helps to break the azeotrope formation between methanol and MTBE. The excess ethylene glycol also inhibits the polymerization of isobutylene. (See Example IV and X.) After refluxing, MTBE is vented off via line 17. The regenerated ethylene glycol is stripped off of methanol and MTBE in stripper section 18 and reboiler 19 and is then recycled back to reactor 1 via line 3.

EXAMPLES II–VIII

A known weight of isobutylene was condensed into a pressure bottle cooled in dry ice-acetone mixture. A mixture containing known weight methanol (MeOH) and known weight ethylene glycol (EG) was added followed by a known weight of an acid catalyst (MSA or Amberlyst 15). The bottle was closed and heated in an oil bath thermostated at 75° C. The pressure initially increased to a maximum, and then fell to a steady value within 15–20 minutes. The bottle was cooled under tap water and opened. The contents were analyzed by HNMR (if MSA was used as catalyst) and by glc (if Amberlyst 15 was used as catalyst). A blank experiment with EG, MeOH and MSA (but no isobutylene) in the pressure bottle took 12–15 min. to attain 75° C. At 75° C., the reaction is effectively complete in about 1.5 minutes. The reactants employed and results of these experiments are summarized in the following Tables I and II.

In Tables I and II, the following abbreviations have the following meanings:
(a) "MeOH" is methanol.
(b) "EG" is ethylene glycol.
(c) "MTBE" is methyl tert-butyl ether.
(d) "ME" is ethylene glycol mono tert-butyl ether.
(e) "DE" is ethylene glycol di-tert-butyl ether.
(f) "ISO" is isobutylene.
(g) "MSA" is methanesulfonic acid.
(h) "AM" is polymeric sulfonic acid manufactured and sold by Rohm Haas Inc. under the trade name Amberlyst 15.
(i) "ratio" is the mole ratio of total divalent oxygen moieties to sulfonic acid moieties in the reaction mixture.
(j) "Acid" refers to MSA or AM.
(k) "—" indicates that the material was not included or observed as a product.

The reactants in these experiments are set forth in the following Table I.

TABLE I

| EX. NO. | Reactants (Mol. Equivalents) | | | | | | |
|---|---|---|---|---|---|---|---|
| | MeOH | ACID | EG | MTBE | ISO | ME | DE |
| II | 1.0 | 0.2 | 0.2 | — | 1.0 | — | — |
| III | 1.0 | 0.4$^a$ | 0.4 | — | 1.0 | — | — |
| IV | — | 1.0 | 1.0 | 0.1 | 1.0 | — | — |
| V | 0.5 | 0.34$^a$ | 0.5 | — | 1.15 | — | — |
| VI | 1.0 | 0.2$^a$ | 0.32 | — | 1.0 | — | — |
| VII | 1.0 | 0.24 | 0.2 | — | 1.0 | .17 | — |
| VIII | 1.0 | 0.34 | 0.14 | 1.0 | 1.0 | .28 | 0.1 |

$^a$These experiments were carried out with both MSA and AM catalyst. The products resulting from these experiments are set forth in the following Table II.

TABLE II

| EX. NO. | Products (Mol. Equivalents) | | | | | | | |
|---|---|---|---|---|---|---|---|---|
| | MTBE | MeOH | ME | DE | EG | ISO | POLYMER | RATIO |
| II | 0.85 | 0.15 | 0.10$^b$ | | 0.10 | 0.05 | — | 7.0 |
| III | 0.75 | 0.25 | 0.20$^b$ | | 0.20 | 0.05 | — | 4.5 |
| IV | 0.1 | trace | 0.25$^b$ | | 0.75 | trace | 0.75$^c$ | 2.1 |
| V | 0.41 | 0.09 | 0.25 | .22 | 0.03 | 0.05 | — | 4.5 |
| VI | 0.73 | 0.27 | 0.11 | .03 | 0.18 | 0.08 | — | 8.2 |
| VII | 0.72 | 0.28 | 0.20 | .07 | 0.10 | 0.08 | — | 7.25 |
| VII | 0.69 | 0.31 | 0.24 | .28 | 0.00 | 0.038 | — | 6.0 |

$^b$Total moles of ME and DE. However, ME accounted for more than 90% of the mixture.
$^c$Represents the number of moles of isobutylene polymerized.

EXAMPLE IX

To a pressure bottle charged with 3 g (0.054 ml.) of isobutylene was attached a Stainless Steel tube containing 1.71 g (0.054 Mol) of MeOH, 3.16 g (0.027 Mol) of EG and 1.3 g (0.013 MOl) of MSA. The bottle was heated in a bath maintained at 75° C. with a thermostat. The Stainless Steel tube was heated to 75° C. using a heating tape. The temperature of the tube was monitored by a thermocouple. Isobutylene in the pressure bottle registered an equilibrium pressure of 80 psig (551.2 kPa). The liquid mixture in the stainless steel tube was dropped into the pressure bottle instantaneously by opening a valve. The pressure dropped to 60 psig (413.4 kPa) after 0.5 min and to 50 psig (344.5 kPa) after 1 min. After 1.5 min. the pressure dropped to 46 psig (316.94 kPa) and remained steady thereafter. Thus, the reaction is effectively complete in about 1.5 minutes to completion.

EXAMPLE X

Several experiments were conducted to demonstrate the effect of the mole ratio of hydroxy moieties in the reaction mixture to sulfonic acid moieties on the amount of monoolefin polymerization. In these exeriments, several stock solutions containing known weights of methyl t-butylether (MTBE) and methanol (MeOH) were prepared in 10 ml conical flasks with ground glass stoppers. A known weight of methanesulfonic acid (MSA) was added to each stock solution and the mixtures were stirred magnetically in an ice-bath for 15 minutes. The mixed solutions from each flask were transferred by means of a syringe into capillary tubes (7.5 cm long, 2 mm diameter and 1 mm thick). The capillary tubes were cooled in dry ice and sealed under vacuum. All capillary tubes were then placed in a previously heated oil bath maintained at constant temperature (70°–100° C.) It took from 3 to 3.5 minutes for the contents inside the capillary tubes to attain the temperature of the bath. The tubes were then removed at different time intervals, cooled in dry ice and opened. The contents were analyzed by 'HNMR. The results are summarized in Table III.

TABLE III

| EXP. NO. | TEMP. °C. | MOLE RATIOS OF | | | % MTBE CONVERTED TO POLYER | MOLE RATIO OF $-OH$ TO $-SO_2H$ |
| --- | --- | --- | --- | --- | --- | --- |
| | | MSA | MeOH | MTBE | | |
| 1 | 70 | 1.0 | 0.36 | 4.72 | 0 | 5.08 |
| 2 | 70 | 1.0 | 0.71 | 3.43 | 0 | 4.14 |
| 3 | 100 | 1.0 | 0.22 | 4.11 | 0 | 4.33 |
| 4 | 90 | 1.0 | 0.75 | 4.0 | trace | 4.75 |
| 5 | 91 | 1.0 | 0.70 | 2.84 | trace | 3.54 |
| 6 | 92 | 1.0 | 0.28 | 2.60 | 13 | 2.88 |
| 7 | 90 | 1.0 | 0.84 | 1.90 | 20.6 | 2.74 |

The equilibration was complete within a minute. The equilibrium mixture contained free isobutylene. The equilibrium concentration of isobutylene, MeOH and MTBE did not change even after 90 minutes, provided that the ratio of moles of total divalent oxygenates to moles of MSA in the mixture is equal to or greater than 3. If this ratio is below 3, the free isobutylene undergoes polymerization shifting the product distribution in favor of polymers. In experiments 6 and 7 in which the mole ratios of oxygenates to MSA are essentially the same, the % of MTBE converted to polymers were 13 and 20.6 respectively. In experiment 6, the conversion was observed at 15 minutes and in experiment 7 was observed at 24 minutes. In all the other experiments, polymers were not observed in more than trace amounts up to 90 minutes.

What is claimed is:

1. In an improved process for the production of methyl ethers of the type in which methanol is reacted with a branched monoolefin in the presence of a catalytically effective amount of an effective acid catalyst, the improvement comprising:
   (a) reacting said methanol with said branched monoolefin in the presence of a polymerization inhibiting amount of one or more diols to form a mixture comprising the methyl ether; and
   (b) separating said methyl ether from said diols by nonazeotropic distillation to provide methyl ether substantially free of said diols.

2. A process according to claim 1 wherein said monoolefin and methanol are reacted in the presence of an excess of said diols.

3. An improved process according to claim 1 which further comprises recycling said diols.

4. In an improved process for the production of methyl ethers of the type in which methanol is reacted with a branched monoolefin in the presence of a catalytically effective amount of an effective catalyst, the improvement comprising the steps of:
   (a) reacting a branched monoolefin with an excess of one or more diols in the presence of an effective acid catalyst to form the corresponding monoether of said diols;
   (b) reacting said monoether with methanol in the presence of an effective acid catalyst to form a mixture comprising said methyl ether and said diols; and
   (c) separating said methyl ether from said mixture by nonazeotropic distillation to provide methyl ether substantially free of said diols or methanol and a residue substantially free of methanol.

5. A process according to claim 4 which further comprises recycling said residue 2 step (c) to step (a).

6. A process according to claim 5 wherein said diols are selected from the group consisting of ethylene glycol and propylene glycol.

7. A process according to claim 1 wherein said monoolefin is reacted with an excess of ethylene glycol.

8. A process according to claim 4 which comprises reacting said branched monoolefin and said diol in counter-current fashion in the presence of said catalyst to provide a bottoms comprising excess diol and the monoether of said diol;
   reacting said bottoms with methanol in counter-current fashion in the presence of said catalyst to provide a mixture comprising said methyl ether, said diol and residual monoether of said diol; and
   separating said methyl ether from said mixture by nonazeotropic distillation to provide the methyl ether substantially free of methanol.

9. A process according to claim 8 wherein said branched monoolefin is isobutylene.

10. A process according to claim 4 which further comprises recycling said bottoms comprising said diol to step (a) of said process.

11. A process according to claim 9 wherein said monoolefin is reacted with excess diols.

12. A process according to claim 10 wherein said diols are selected from the group consisting of ethylene glycol and propylene glycol.

13. A process according to claim 11 wherein said diol is ethylene glycol.

* * * * *